United States Patent [19]
Raynie

[11] Patent Number: 5,662,630
[45] Date of Patent: Sep. 2, 1997

[54] BIODEGRADABLE URINE COLLECTION DEVICE

[75] Inventor: Arthur D. Raynie, San Antonio, Tex.

[73] Assignee: Peapod Systems, Inc., San Antonio, Tex.

[21] Appl. No.: 199,096

[22] Filed: Feb. 22, 1994

[51] Int. Cl.[6] ........................................ A61F 5/44
[52] U.S. Cl. ........................ 604/349; 604/353; 4/144.2
[58] Field of Search ................................. 604/349–353, 604/322–326, 265; 4/144.3, 144.2

[56] References Cited

U.S. PATENT DOCUMENTS

| | | | |
|---|---|---|---|
| 4,608,046 | 8/1986 | Towfigh | 4/144.3 |
| 4,756,029 | 7/1988 | Zieve et al. | 4/144.2 |
| 4,769,019 | 9/1988 | Kerwin | 604/323 |
| 4,790,834 | 12/1988 | Austin | 604/349 |
| 4,820,291 | 4/1989 | Terauchi et al. | 604/349 |
| 4,846,816 | 7/1989 | Manfredi | 604/323 |
| 4,868,024 | 9/1989 | Cross et al. | 428/35.2 |
| 5,300,049 | 4/1994 | Hogan | 604/317 |
| 5,318,549 | 6/1994 | Yang | 604/349 |
| 5,354,132 | 10/1994 | Young et al. | 4/144.2 |
| 5,404,999 | 4/1995 | Bednar | 206/204 |
| 5,409,474 | 4/1995 | Fleeman-Hardwick | 604/349 |

FOREIGN PATENT DOCUMENTS

| | | | |
|---|---|---|---|
| 2936622 | 3/1981 | Germany | 4/144.2 |
| 9008525 | 8/1990 | WIPO | 4/144.2 |

*Primary Examiner*—John G. Weiss
*Assistant Examiner*—Mark O. Polutta
*Attorney, Agent, or Firm*—Gunn, Lee & Miller, P.C.

[57] ABSTRACT

A urine collection device, including a biodegradable bag for storage of the urine therein and a biodegradable engagement member for engaging the genitals of the user, the biodegradable bag having within the bag a means to disperse the urine received from the biodegradable engagement member into the interior of the bag.

7 Claims, 8 Drawing Sheets

BIODEGRADABLE URINE COLLECTION DEVICE

FIELD OF THE INVENTION

Urinary collection devices more specifically, a biodegradable, disposable urinary collection device.

BACKGROUND OF THE INVENTION

Urine collection devices have their most obvious use in the health care industry. However, other areas of human endeavor outside the health care industry also find uses for urine collection devices. Hunters, pilots, boaters, any travelers/truck drivers, handicapped individuals would also find, under certain circumstances, that an easy to use, disposable urine collection device would be advantageous or necessary. Moreover, given the current concern for the huge amount of waste products produced by our society—for example the enormous load that disposable diapers puts on land fills—the need for a biodegradable urine collection device would also appear to be important. Last, a urine collection device, in addition to being biodegradable and disposable, must be both easy to use and easy and inexpensive to manufacture. It provides little commercial advantage to possess all the other qualities of a good urine collection device if it is prohibitably expensive to the consumer.

Four the advantages of convenience and safety in collection and storage of the urine, the bag or collection vessels of the urine collection devices should contain an element or material that will react with the urine to convert the urine from a fluid to a gel. However, dispersion of the urine into the bag in reaction with the gelatinizing reagent may clog the tube transporting the urine into the bag. Thus, it is advantageous to provide in the urine collection device, a means to introduce the urine into the collection bag or vessel without the possibility of clogging the transport tube.

Urine collection devices require an effective seal between the genitalia and the device itself to prevent leakage and to maintain comfortable and sanitary conditions during use. Moreover, such a genital engagement member must possess the same qualities of biodegradability and ease of manufacturer that are required of the bag and the tube of the end collection device. That is, the urine collection device should be 100% biodegradable.

Added convenience is provided for by including the urine collection device as part of a kit, the kit including the urine collection device for storage before and after use and a water-proof, self-sealing biodegradable bag and, including in the bag, a biodegradable privacy skirt to be used for shielding the private parts during use.

Heretofore, the market has lacked a urine collection device that is inexpensive to manufacture, easy to use, disposable and biodegradable. Thus, it is an object of the present invention to provide a urine collection device, in male and female models, which is inexpensive to manufacture, easy and effective to use, biodegradable and disposable.

SUMMARY OF THE INVENTION

This and other objects are provided for in a urine collection device having a biodegradable bag for the collection and storage of urine therein and also a biodegradable engagement member for engaging the genitals of the user and capable of transporting urine to the biodegradable bag.

It is another object of this invention to provide for a urine collection device having a biodegradable bag including a means to gelatinize the urine collected within the bag.

It is another object of this invention to for a urine collection device having a biodegradable bag with a means to disburse the urine through multiple orifices into the interior of the bag.

This and other objects are provided for in a urine collection device with a biodegradable engagement member designed to conform to the male or female genitals.

This and other objects are provided for in a urine collection device with a biodegradable engagement member for adjustably and releasably grasping the shaft of the male genitals.

This and other objects are provided for in a urine collection device having walls defining a slotted funnel having, a first opening in the funnel for receipt of the male genitals therein and a second opening for transportation of the urine into a biodegradable bag.

This and other objects are provided for in a urine collection device having a biodegradable bag comprised of paper having a leak-proof coating and further having a heat activated adhesive means on the surface thereof.

Last, this and other objects are provided for in a urine collection device having a privacy skirt, as well as a means to wrap the urine collection device and for ease of disposal.

DETAILED DESCRIPTION OF THE PREFERRED EMBODIMENT

Figures 1A, 1B, 1C, 1D:
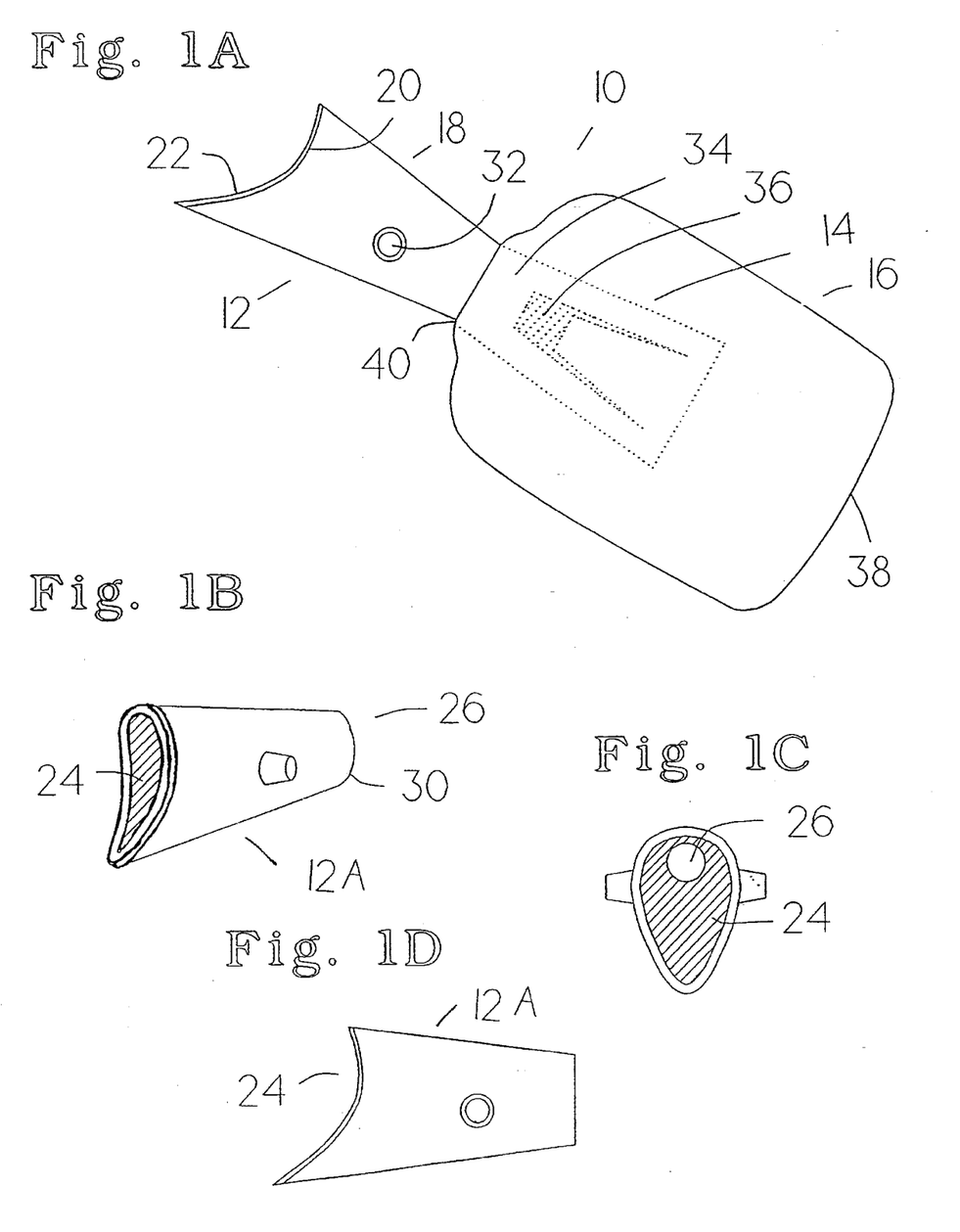
FIG. 1A is a side elevational view of the engagement member and dispersal means, a portion of applicant's present invention.
FIG. 1B is a perspective view of the female engagement member of applicant's present invention.
FIG. 1C is a front elevational view of the female engagement member of applicant's present invention.
FIG. 1D is a side elevational view of the female engagement member of applicant's present invention.

FIGS. 1A–D illustrate the urine collection device (10) of applicant's present invention. As can be seen in FIG. 1A, urine collection device (10) is comprised of a female engagement member designed to fit flush against the exterior of the vagina so as to create a seal between the user and the urine collection device. Urine collection device (10) also contains a dispersal means for dispersing the urine within a leak-proof, biodegradable collection bag (16).

Turning now to the female engagement member (12a), it is seen to be comprised of a body portion (18) having a perimeter (20) upon which is attached a cushion (22). FIGS. 1B and 1C in particular illustrate the perimeter (20) having an oval shape in front view (FIG. 1C) in a crescent shape and side view (FIGS. 1A and 1D). More specifically, perimeter (20) defines a front opening (24) of body (18), which is configured in size and shape to seal against the female genitalta with cushion (22) designed to create a leak-proof seal between the skin and female engagement member (12a).

Body (18) of female engagement member (12a) is conical in shape with front opening (24) being larger than the opposite end of a rear opening (26). As seen in FIG. 1C, rear opening (26) is more generally circular in shape and has walls (30) defining rear opening (26). Also apparent from the drawings is handle (32) on opposite sides of body (18) of female engagement member (12a). Handles (32) provide a convenient means for positioning and maintaining female engagement member (12a) against the skin when in use, and may be molded from the same material that forms body 18).

FIG. 1A also illustrates manner in which dispersal means (14) is positioned within collection bag (16), and is comprised of side walls (34) having cut-outs defined by side wall opening (36). Bag (16) is sealed around a perimeter (38) and joins dispersal means (14) at a neck (40).

Urine collected during use is transported through female engagement member (12a) from front opening (24) to rear opening (26) and carried into dispersal means (14) where it exits therefrom into the interior of bag (16) through side wall opening (36).

Dispersal means (14) functions to introduce the urine into the interior of collection bag (16) along a contract boundary having as large as possible an area. Details of dispersal means (14) will be appreciated with reference too FIGS. 3A–3B below.

It can be readily appreciated that the details of the construction and design of female engagement member (12a) will differ from the design of a male engagement member. These differences may be appreciated with reference to FIGS. 2A–2G. More specifically, FIGS. 2A–2G illustrate male engagement member (12b) comprised of a body shaped generally to define a cone (42), the cone (42) having walls (44) defining slot (46) in the body of cone (42). Walls (44) of cone (42) further define front opening (48), the front opening (48) having perimeter (50). Front opening (48) of cone (42) has at the opposite end thereof rear opening (52). Thus, male engagement member (12b) is defined by cone (42) with front opening (48) larger than rear opening (52); the latter of which is a closed circle.

Figure 2A:
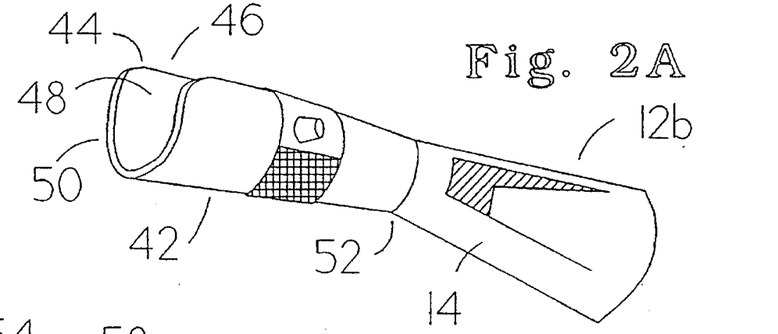
FIG. 2A is a perspective view of the male engagement member and dispersal means of applicant's present invention.
Figure 2B:
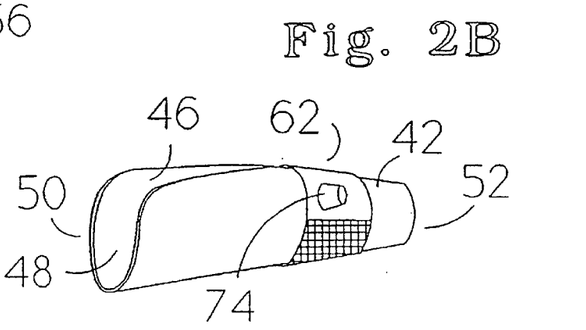
FIG. 2B is a perspective view of the male engagement member of applicant's present invention in an open position.
Figure 2C:
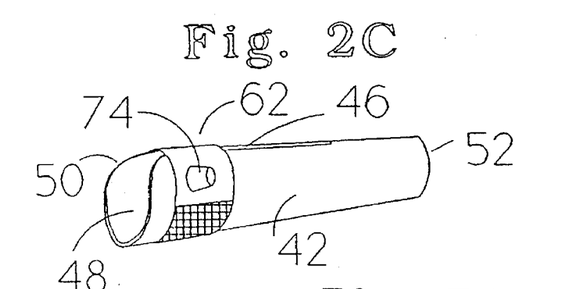
FIG. 2C is a perspective view of the male engagement member of applicant's present invention in a closed position.
Figure 2D:
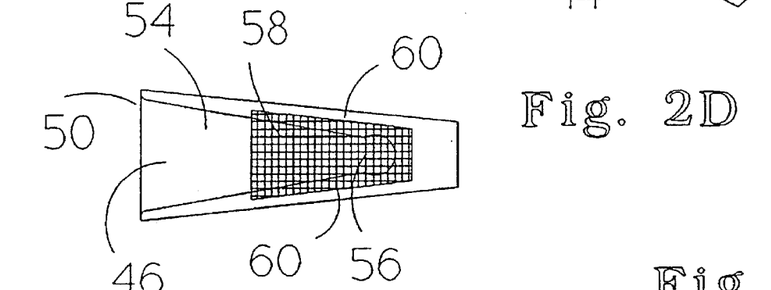
FIG. 2D is a top elevational view of the male engagement member of applicant's present invention in an open position.

Turning now to FIG. 2D, it is seen that slot 46 is comprised of mouth portion (54) where walls (44) engage perimeter (50). Slot (46) tapers from mouth (54) to apex (56). Between mouth (54) and apex (56) is cover (58), typically impervious to the passage of fluids which is attached, typically by gluing along opposite perimeters thereof to walls adjacent slot (46), specifically wall (60).

Figure 2E:
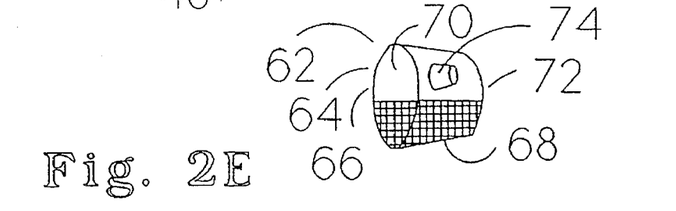
FIG. 2E is a perspective view of the male engagement member of applicant's present invention.
Figure 2F:
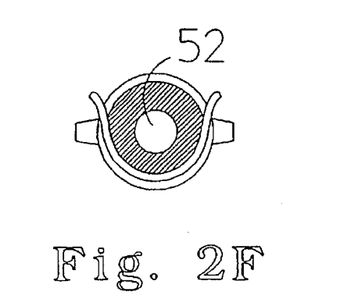
FIG. 2F is an elevational view of the front and of the male engagement member of applicant's present invention in an open position.
Figure 2G:
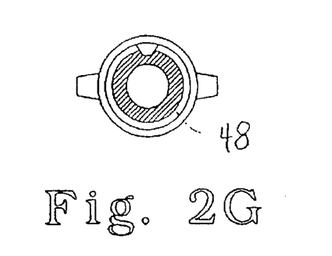
FIG. 2G is an elevational view of the front end of the male engagement member of applicant's present invention in a closed position.

Turning now to FIGS. 2B, 2C and 2E, it is seen that collar (62) is designed to engage the walls of cone (42) of male engagement member (12b) as set forth in FIGS. 2B and 2C. Collar (62) is conically shaped having a body (64), body (64) being comprised of an inelastic portion (66) and elastic portion (68) joined in such a manner as to define a regular cone shape having a front opening (70) and a rear opening (72), the former having a larger diameter than the latter. Handles (74) on inelastic portion (66) of body (64) are used to manipulate collar (62) in a manner set forth below.

FIGS. 2B and 2C illustrate the manner in which collar (62) engages cone (42) to comprise male engagement member (12b). More specifically, FIGS. 2B and 2C illustrate the manner in which front opening (70) of collar (62) is slipped over rear opening (52) of cone (42) with collar (62) sliding longitudinally towards front opening (48). Moreover, in FIG. 2C it is seen how movement of collar (62) longitudinally from rear opening (52) towards front opening (48), will cause the width of slot (46) to narrow, especially in the area of mouth (54).

In use, male engagement member (12b) is placed surrounding the male penis with the collar in a withdrawn position, similar to illustration in FIG. 2B. Sliding collar (62) longitudinally towards a closed position as illustrated in FIG. 2C will allow the width of mouth (54) to decrease and contract around the shaft of the male genitals. Elastic portion (68) of collar (62) will allow collar (62) to expand in diameter once a snug fit is affected between mouth (48) and the shaft of the male genitals to create a snug fit, but one which is loose enough to permit a normal flow of urine through the shaft of the penis.

Thus, male engagement member (12b) provides a snug fit to the shaft of the male genitals and is further capable of accommodating genitals of differing dimensions, specifically in differing widths. That is, the male genitals of a larger width, the collar (62) would reach snug fit and elastic portion (68) would expand before the position illustrated and FIG. 2C is reached, providing mouth (54) was a larger width. It is further seen that the use of impervious collar (58) protects from the leakage of urine through slot (46) during use. The funnel shape of cone (42) directs urine to flow through rear opening (52) which is attached to dispersal means (14) as illustrated in (12a).

FIGS. 1B–1D and FIGS. 2A–2D illustrate the manner in which urine collection device (10) is provided with an engagement member designed to accommodate the anatomical differences between the male and female of the species and further is designed to fit the anatomical difference between the variety found within the individuals of the male species. Both engagement members are designed to be leak-proof. Both engagement members are designed to channel urine through a cone-shaped body having a small opening at the distal end thereof. These small openings, illustrated as rear opening (26) in FIG. 1B and rear opening (52) in FIGS. 2B and 2C engage dispersal means (14) to transport the urine thereinto.

Figure 3A:
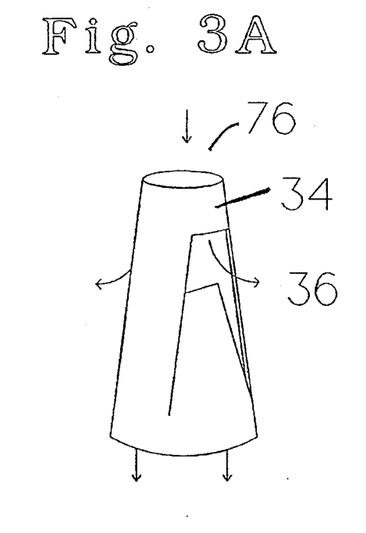
FIG. 3A is a perspective view of the dispersal means of applicant's present invention.
Figure 3B:
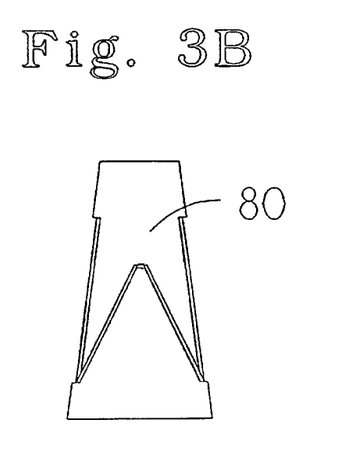
FIG. 3B is a cut-away view inside elevation of the dispersal means of applicant's present invention.
Figure 3C:
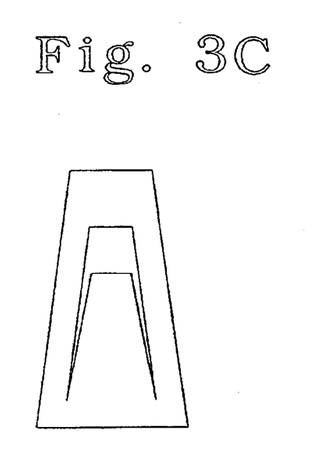
FIG. 3C is a side elevational view of the dispersal means of applicant's present invention.
Figure 3D:
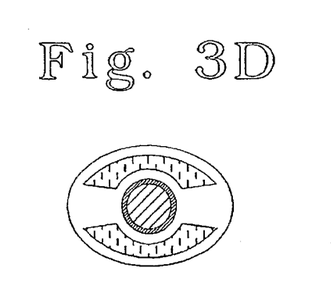
FIG. 3D is a top elevational view of the dispersal means of applicant's present invention.
Figure 3E:
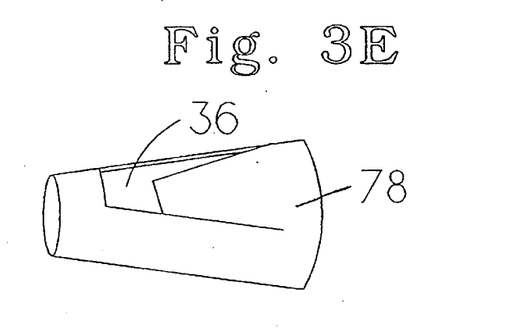
FIG. 3E is a perspective side view of the dispersal means of applicant's present invention.

FIGS. 3A–3F illustrate the design, construction and features of dispersal means (14). Dispersal means (14) is shaped generally as a cone having front opening (76) and rear opening (78), the two openings joined by side walls (34). Moreover, it can be seen with reference to FIG. 3D how dispersal means (14), specifically front opening (76) and rear opening (78) have ellipsoid rather than circular shapes. That is, front and rear openings (76) and (78) respectively do not have uniform radii as curvature, rather form ellipsis with major and minor axis. The purpose for squeezing dispersal means (14) into an oval ellipsoid or shape when viewed from atop or bottom is to provide an easy fit within collection bag (16) (See FIG. 1A) and to provide a low profile when inserted into the collection bag (See FIG. 4F). Side walls (34) of dispersal means (14) define an enclosed portion (80). Urine will pass from the engagement member of urine collection device (10) into front opening (76). Urine must then flow through enclosed portion (80) to reach and make contact with the interior portion of collection bag (16). The arrows set forth in FIGS. 3A illustrate the passage of urine from enclosed portion (80) to the exterior and beyond dispersal means (14), specifically through side wall openings (36) or through rear openings (78). The purpose of dispersal means (14) is to provide multiple paths for which urine can pass into the interior of collection bag (16). That is, without dispersal means (14), the engagement member of urine collection device would simply engage the neck (40) of collection bag (16) and dump all the urine into the bag through rear opening (26). The problem often arises, however, when a means to gelatinize or change the phase of the liquid urine into a gel or a more solid phase is used or placed within collection bag (16). Reaction of a gelatinizing means with the urine when a simple orifice is provided between engagement member feeding the bag, will clog up the single orifice where gelatinization takes place at that location. Jamming up the only orifice will cause the urine to back up into the engagement member and cause the urine collection device to leak or spill over.

Figure 3F:
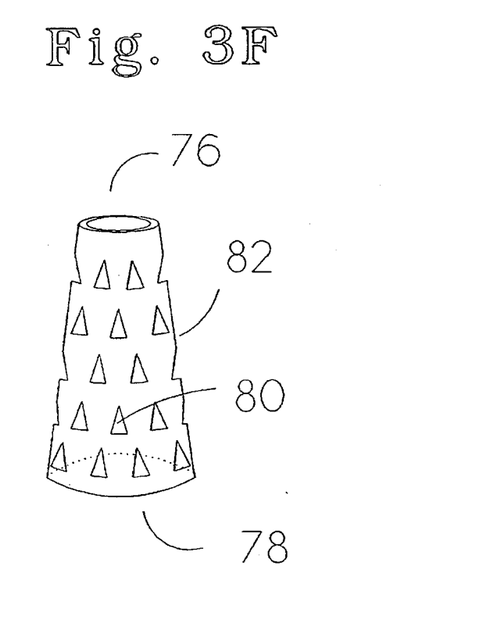
FIG. 3F is a side elevational view of an alternate preferred embodiment of the dispersal means of applicant's present invention.

Dispersal means simply provides for receipt of urine into the interior of the bag through a simple orifice by dispersal into the interior of the bag through multiple orifices before contact is made with gelatinization agent within the bag. FIG. 3F illustrates an alternate preferred embodiment of dispersal means (14) having, instead of side wall opening (36), numerous multiple orifices (82) through which urine, introduced into front opening (76) may be dispersed into collection bag (16).

Figure 4A:
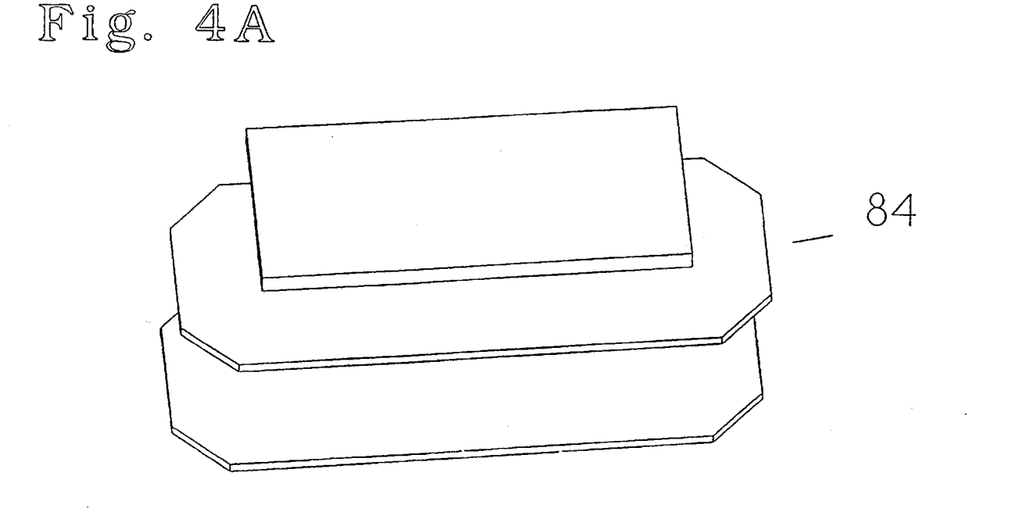
FIG. 4A is an exploded perspective view of the 3-plies forming the sheet of the bag of applicant's present invention.
Figure 4B:
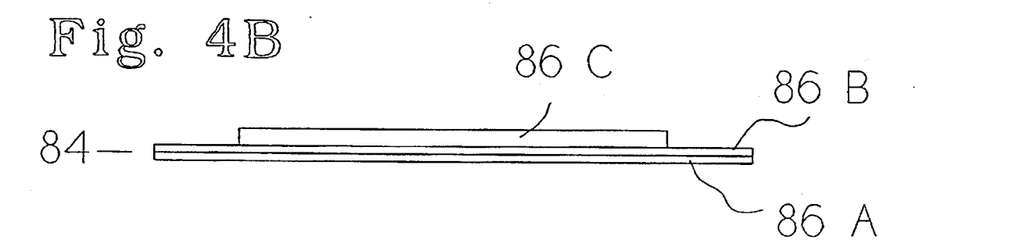
FIG. 4B is a side elevational view of the 3-ply of the sheet forming the bag of applicant's present invention.
Figure 4C:
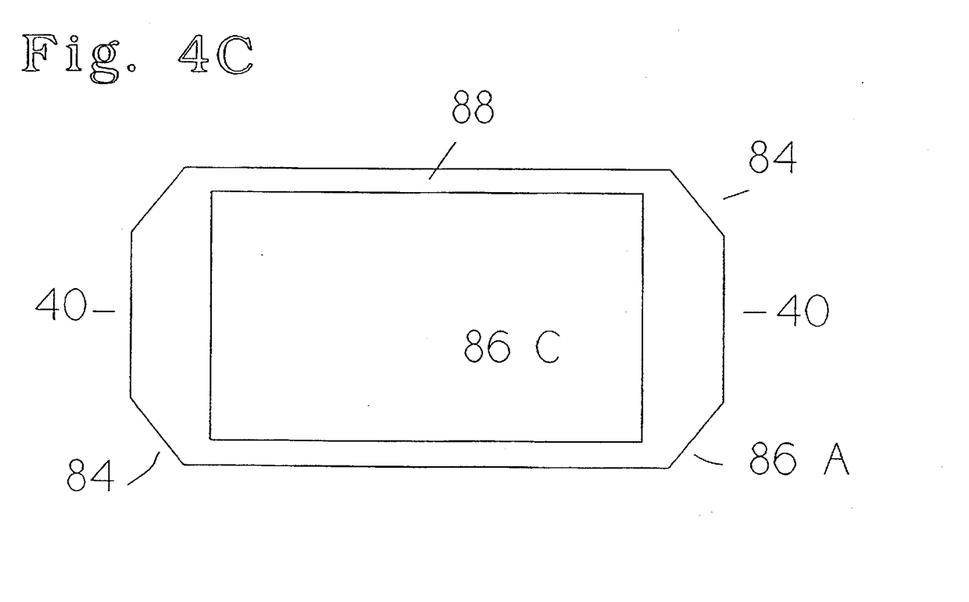
FIG. 4C is a top elevational view of the sheet that is used to form the bag of applicant's present invention.
Figure 4D:
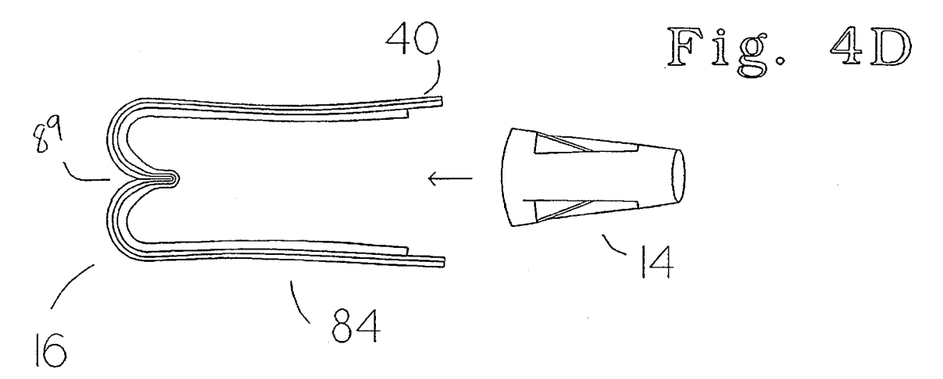
FIG. 4D is a side elevational view in exploded form showing the sheet of the bag of applicant's present invention folded over and the dispersal means ready for insertion therein.
Figure 4E:
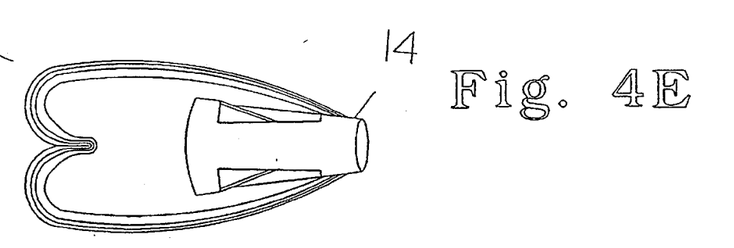
FIG. 4E is the cut-away view of the bag applicant's present invention showing the dispersal means in the interior of the bag.
Figures 4F, 4G:
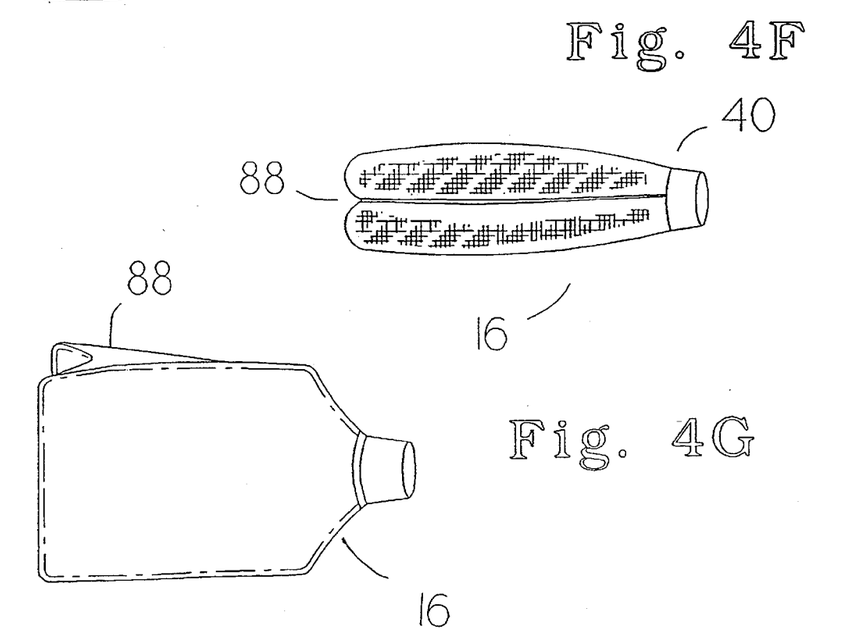
FIG. 4F is a side elevational view of the exterior of the bag of applicant's present invention with the dispersal means inserted.
FIG. 4G is a top elevational view of the bag of applicant's present inventions with the dispersal means inserted and sealed therein. Top and bottom views are the same.
Figure 5A:
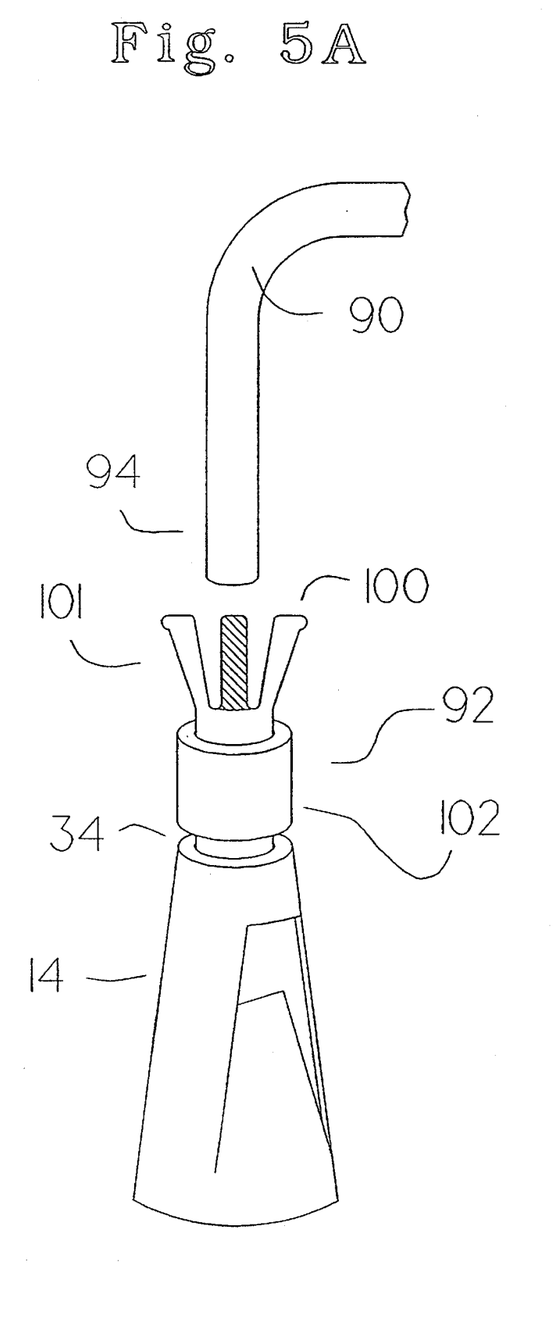
FIG. 5A is a perspective view of an embodiment of applicant's present invention providing for the insertion of a tube into the dispersal device of the dispersal means.
Figure 5B:
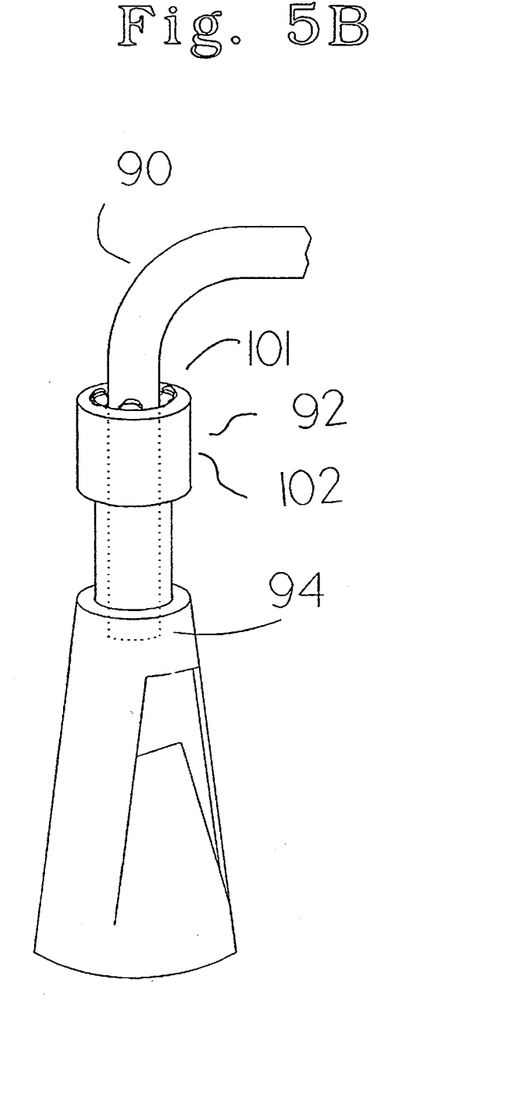
FIG. 5B is a perspective view of the dispersion means showing the tube inserted therein.
Figure 5C:
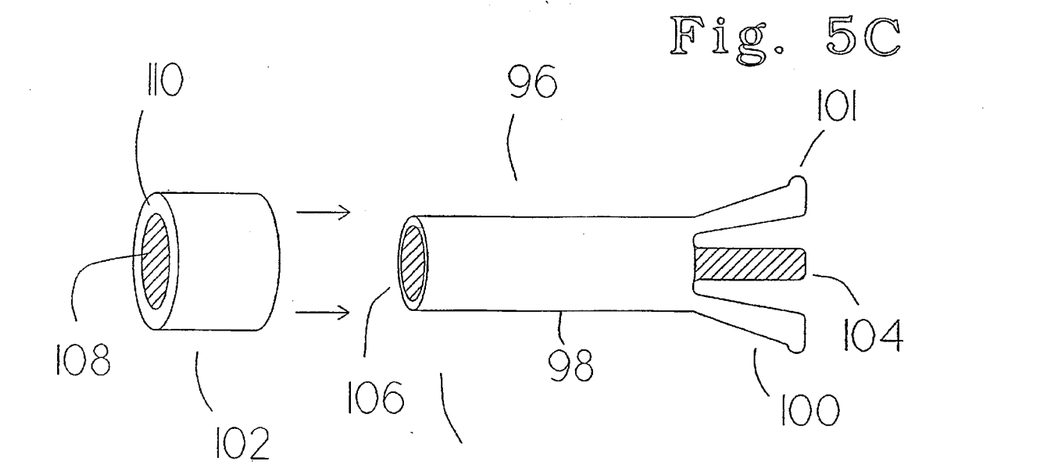
FIG. 5C is an exploded of a means for gripping the tube for insertion into the dispersal means of applicant's present invention in perspective.
Figure 5D:
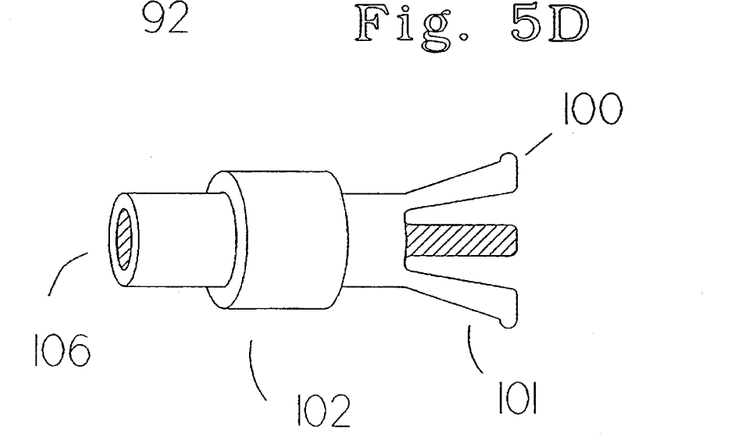
FIG. 5D is a second view in perspective of a means for gripping the tube for insertion into the dispersal means of applicant's present invention.
Figure 5E:
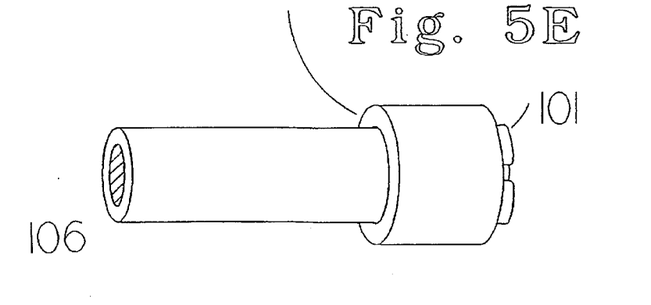
FIG. 5E is a third view in perspective of a means for gripping the tube for insertion into the dispersal means of applicant's present invention.
Figure 5F:
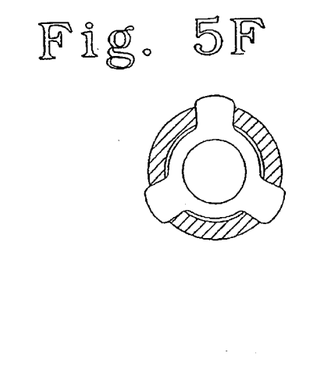
FIG. 5F is an end view in elevation of the means for gripping the tube as illustrated in FIG. 5D.
Figure 5G:
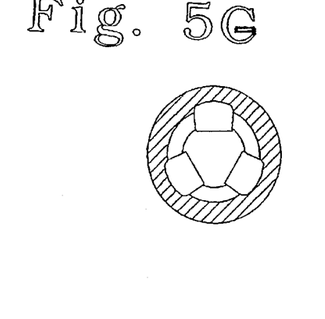
FIG. 5G is an end view in elevation of the means for gripping the tube as illustrated in FIG. 5E.

FIGS. 4A–4G illustrate the details and manner of construction of collection bag (16) of the urine collection device (10). At the outset, it is seen in a particular reference to FIG. 4A, how collection bag is comprised of sheet (84), folded into a bag shape. Specifically, sheet (84) is comprised of three plies (86a), (86b) and (86c). Turning now to FIG. 4A is seen how outer ply (86a), middle ply (86b) and inner ply (86c) are joined as single sheet (84). More specifically, outer ply (86a) is comprised of a tough, durable, light-weight, tear-resistant tissue of polyester weave material. It is joined to inner-ply (86c) by middle ply (86b) which is typically made of white crepe tissue (E1002). Inner ply (86c) is made of super absorbent polymer and wood pulp fiber, which has the properties capable of, when reacting with urine, gelatinizing the normally fluid urine. The materials joined by an adhesive glue such as 3M 2262, which comes as an aerosol spray, and, including its adhesive properties, renders sheet 84 waterproof.

Glue is used to join the sheets, such that when sheet (84) is laid out such as illustrated in FIG. 4C, a perimeter exists beyond the borders of inner-ply (86c), here illustrated as perimeter (88). This occurs so that when sheet (84) is folded over in the manner illustrated in FIG. 4D, and following insertion of dispersal means about neck (40) applying heat to perimeter (88) will seal the bag along the perimeter and around neck (40), where dispersal means (14) is sealed within collection bag (16).

The outer layer may be made from Criterion™ spun-lace fabric available from the Materials Division of Johnson & Johnson. The middle layer may be constructed from crepe tissue available also from the Materials Division of Johnson & Johnson. The inner layer is a composition created by a mixture of two materials. The first is Zap™, a super absorbent polymer (POLIACRYATE) manufactured by Stockhausen of New Jersey. The second material is common wood pulp fiber manufactured by, among others, Weyerhaeuser. These two mixtures are mixed in the ratios of approximately 10–50% wood pulp, typically 10–20% depending upon the type of super absorbent polymers are used, so as to avoid fast absorption locally in places Where moisture contacts the mixture.

FIGS. 5A–5E illustrate an alternate preferred embodiment of urine collection device (10), specifically an embodiment for use with a tube (90). Tube (90) engages dispersal means (14) through connecting member (92). Tube (90) has tube end (94). Connecting member (92) is comprised of cylindrical sleeve (96) having a cylindrical body (98) and splayed legs (100). Splayed (100) have bald feet (101) at their terminus thereof. Connecting member (92) includes collar (102) capable of sliding onto cylindrical sleeve (96) in the manner set forth in FIGS. 5C, 5D and 5E. The interior diameter of cylindrical body (98) is just slightly larger than tube end (94) to create a snug fit between the inner walls of cylindrical body (98) and the exterior of tube end (94). When tube end (94) is inserted into distal end (104) of connecting member (92) until snug, collar (102) is inserted over proximal end (104) of sleeve (96). A circular opening (108) of collar (102) snugly engages cylindrical body (98) as collar (102) slips over proximal end (106). Further movement longitudinally will cause walls (110) defining circular opening (108) to exert pressure against proximal ends of splayed legs (100). Continual urging of collar (102) longitudinally towards bald feet (101) will squeeze splayed legs (100) against the outer surface of tube (90) in the manner illustrated in FIGS. 5B and 5E, thus gripping tube end (94) in place through the pressure of walls (110) urging splayed legs (100) against tube (90). Bald feet (101) are sufficiently large to prevent the inadvertent passage of collar (102) beyond bald feet (101) as the collar is urged longitudinally towards distal end (104). Proximal end (106) of cylindrical body (98) is glued to side walls (34) defining front opening (76) of dispersal means (14). Thus, FIGS. 5A–5E illustrate a manner in which an interconnect member or other means may be provided between dispersal means (14) and a permanent tube (90), such that urine collection device (10) may, in a preferred embodiment used with a permanent (non-disposable) tube to create a water-proof seal between tube end (94) and urine collection device (10). In the embodiment described in FIGS. 5A–5B, an engagement member is not part of the disposable, biodegradable urine collection device (10). This may be the case, for example, in a permanently or acute care patient, which has a catheter carrying fluids through tube end (94), which is affixed to the patient for a use over a number of days or weeks. A nurse or other health care attendant would then simply attached, using connecting member (92), urine collection device (10) to tube end (94), after use, urine collection device (10) being disposable as set forth and provided for in other areas of the specifications.

Figures 6A, 6B, 6C:
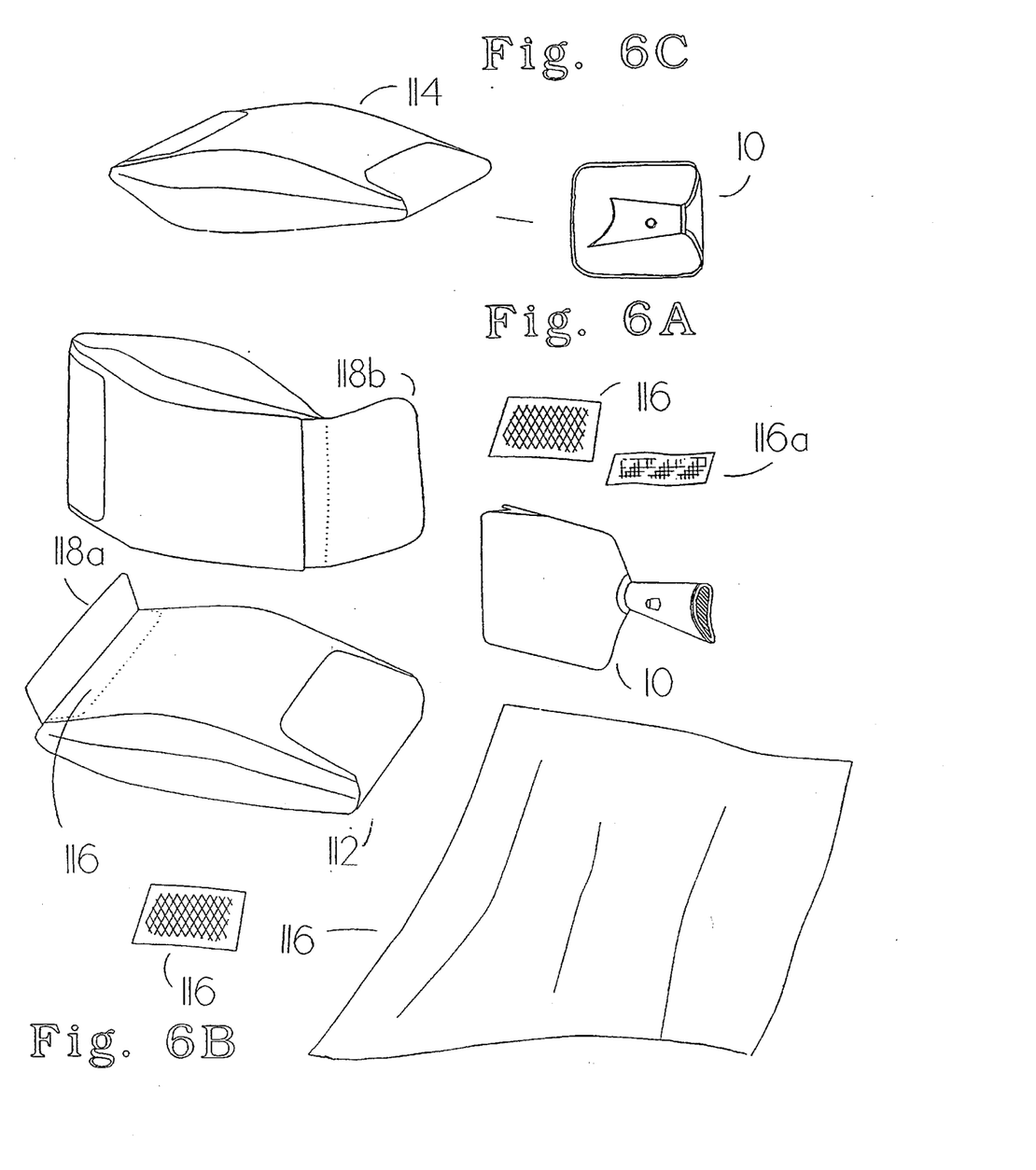
FIG. 6A illustrates applicant's invention as a kit having the urine collection device, privacy skirt and a bag for containing these two items therein.
FIG. 6B is a perspective view of the privacy skirt and bag of applicant's present invention.
FIG. 6C is a perspective view showing the urine collection device for insertion within the bag of applicant's present invention.

More particularly, FIGS. 6a–6c illustrate kit (112) comprised of urine collection device (10), enclosed within biodegradable fabric container (114) and including biodegradable fabric opaque skirt (116) and a clean-up wipe (116a), preferably damp with a mild soap or a mild external antiseptic contained therein. Privacy skirt (116) is typically unfolded for use as illustrated in FIG. 6B where an edge of (116) is sealed between foldable flap (118a). Foldable flap (118b) is typically used to remove unused urine collection device (10) and privacy skirt (116) therefrom for use.

Following use, privacy skirt (116) is folded and inserted into fabric container (114) along with urine containing urine collection device (10). Resealable flap (118b) is then folded over to seal up urine collection device, folded as illustrated in FIG. 10C for insertion into container (114) for proper disposal. It is noted that all of the components of kit (112) as well as all of the components of urine collection device (10) are biodegradable such that one merely needs to dispose urine collection containing kit (112) after use.

The table below sets forth descriptions of various biodegradable materials for use with applicant's invention, along with a source name and/or location.

| DESCRIPTION | SOURCE |
| --- | --- |
| Dispersal means (14), body (18), cushion (22). | 14 = pressed or molded wood pulp fiber and/or recycled paper fiber<br>18 same as 14<br>22 heavy felt material |
| Walls (30) of dispersal means (14). | Thick, made from pressed or molded wood pulp fiber and/or recycled paper fiber. |
| Cone (42) of male engagement member (12b) | Made from pressed or molded wood pulp fiber and/or recycled paper fiber. |
| Cover (58) of male engagement (12b). | Made from pressed or molded wood pulp fiber and/or recycled paper fiber. |
| Body (64) of collar (22). | Made from pressed or molded wood pulp fiber and/or recycled paper fiber. |
| Inelastic portion (66) of body (64) | Made from pressed or molded wood pulp fiber and/or recycled paper fiber. |
| Elastic portion (68) of body (64) | Heavy duty stretchable crepe paper. |
| Handles (74). | made from pressed or molded wood pulp fiber and/or recycled paper fiber (may be integral with body (18) or cone (42)). |
| Outer ply (86a) of sheet (84). | Criterion ™ by the Materials Division of Johnson & Johnson. Tissue and polyester weave. |
| Middle ply (86b) of sheet (84). | White crepe tissue E1002 or E912 by the Materials Division of Johnson & Johnson. |
| Inner ply (86c) of sheet (84). | Super exorb.polymer and wood pulp material. |
| Connecting member (92). | Made from pressed or molded wood pulp fiber and/of recycled paper fiber. |
| Glue for connecting dispersal means to either connecting member (92) or engagement nember. | 3M2262/or any non-toxic heat activated glue or adhesive spray. |
| Fabric container (114). | Heavy ply waxed or sealer coated paper bag materials or Criterion ™. |
| Privacy skirt (116). | Paper netting/paper towel type or Criterion ™. |

The engagement members and the dispersal means described above (with the exception of the cushions and the elastic crepe) can be formed in one of three ways. First, a paper pulp is injected into a heated mold, which dehydrates the pulp. Secondly, the paper pulp may be injected as described except the pulp is formed from recycled paper products which have been cleaned or processed to get rid of ink, or other waste materials. Third, a worker may manually lay out pulp material into a male/female cavity mold which is then cold pressed to squeeze the water out. The resulting product of any of the foregoing three processes will provide for a biodegradable device.

Terms such as "left," "right," "up" "down," "bottom," "top," "front," "back," "in," "out," and like are applicable to the embodiments shown and described in conjunction with the drawings. These terms are merely for purposes of description and do not necessarily apply to the position or manner in which the invention may he constructed for use.

Although the invention has been described in connection with the preferred embodiment, it is not intended to limit the invention's particular form set forth, but on the contrary, it is intended to cover such alternatives, modifications, and equivalences that may he included in the spirit and scope of the invention as defined by the appended claims.

What is claimed is:

1. A urine collection device for use with a urine carrying tube, the urine collection device comprising:

a bag for storage of the urine therein;

engagement means capable of releasably engaging the urine carrying tube, wherein said engagement means comprise a multiplicity of leg members moveable between a splayed, normally open position out of engagement with the tube and a closed position for engaging the tube, wherein said engagement means further comprises a sliding collar for cooperating with the leg members, urging the leg member from the normally open position to the closed position for engagement with the tube; and dispersal means having a multiplicity of orifices therein through which to disperse urine received from the urine carrying tube, into the interior of said bag.

2. The urine collection device as set forth in claim 1 further comprising a privacy skirt.

3. The urine collection device as set forth in claim 1 further comprising means to contain said bag and engagement member.

4. The urine collection device as set forth in claim 1, wherein said bag contains means to gelatinize the urine.

5. The urine collection device as set forth in claim 1, wherein said bag is comprised of paper.

6. The urine collection device as set forth in claim 5, wherein said bag is comprised of paper and said paper is treated with a leak-proof coating.

7. A urine collection device for a human male, the device comprising a bag for storage of the urine therein, wherein said bag includes a means to gelatinize the urine;

a engagement member for engaging the genitals of the user and capable of transporting urine to said bag wherein said engagement member is comprised of walls dimensioned to conform to the male penis, and capable of releasably grasping the shaft of the male penis for adjustably fitting penises of various sizes, the walls of said engagement member defining a slot capable of expanding and contracting in width, and a funnel, the funnel having a first perimeter defining a first opening and a second perimeter defining a second opening in the funnel shaped walls, the first opening having a greater diameter than the second opening, the slot of said engagement member joining the first perimeter, the first opening designed for receipt of the penis therethrough, the second opening for delivering urine into dispersing means;

said dispersal means having a multiple of orifices therein for accepting the urine from said engagement member and dispersing the urine into the interior of said bag;

means capable of engaging the funnel of said engagement member to adjust the width of the slot of said member for adjustably varying the diameter of the first opening;

a privacy skirt; and container means to contain said engagement member and said bag for disposal.

* * * * *